United States Patent [19]
Gengnagel

[11] 3,933,887
[45] Jan. 20, 1976

[54] PROCESS FOR PREPARING 4-AMINO-2,5-DIALKOXYBENZONITRILES

[75] Inventor: Kurt Gengnagel, Offenbach (Main), Germany

[73] Assignee: Hoechst Aktiengesellschaft, Frankfurt am Main, Germany

[22] Filed: July 22, 1974

[21] Appl. No.: 490,414

[30] Foreign Application Priority Data
July 26, 1973 Germany............................ 2337951

[52] U.S. Cl............................................. 260/465 E
[51] Int. Cl.²..................................... C07C 121/78
[58] Field of Search ................................ 260/465 E

[56] References Cited
UNITED STATES PATENTS
3,423,412   1/1969   Taylor et al. .................. 260/465 X

*Primary Examiner*—Lewis Gotts
*Assistant Examiner*—Dolph H. Torrence
*Attorney, Agent, or Firm*—Connolly & Hutz

[57] ABSTRACT

A process for preparing 4-amino-2,5-di-($C_1$-$C_4$) alkoxybenzonitriles which comprises brominating 1-acylamino-2,5-dialkoxybenzenes, converting the 1-acylamino-2,5-dialkoxy-4-bromobenzenes so obtained by the reaction with copper-I-cyanide to the 4-acylamino-2,5-dialkoxy-benzonitriles and subsequently hydrolyzing the acylamino group; the known compounds are prepared by means of this process in better yields and in a technically simpler way.

1 Claim, No Drawings

PROCESS FOR PREPARING 4-AMINO-2,5-DIALKOXYBENZONITRILES

The present invention relates to a process for preparing 4-amino-2,5-dialkoxybenzonitriles.

Object of the invention is an improved process for the preparation of 4-amino-2,5-dialkoxybenzonitriles, especially of those in which the alkoxy groups carry 1 to 4 carbon atoms.

The 4-amino-2,5-dialkoxybenzonitrile is available in commerce in the form of its hydrochloride and as stabilized diazonium salt under the name of Echtbordo BD Base of Echtbordosalz BD and is used according to the methods of the ice-colortechnique (cf. Color Index, Third Edition 1971, C.I. 37 170, C.I. Azoic Diazo Component 40) for the preparation of water-insoluble azo dyestuffs on the fiber.

The industrial preparation occurs by nitration of 1-benzoylamino-2,5-dimethoxybenzene, hydrolysis in aqueous alcohol to the 1-amino-2,5-dimethoxy-4-nitrobenzene, reaction by means of the Cyan-Sandmeyer reaction to the 4-nitro-2,5-dimethoxy-benzonitrile and following sodium sulfide reduction to the 4-amino-2,5-dimethoxybenzonitrile (cf. BIOS 1149, page 44 et seq.)

This process leads over 4 stages and gives a total yield of 58 %. In this process the alcohol must be recovered from the saponification, and the excess cyanide from the Cyan-Sandmeyer reaction must be depoisoned. Moreover, the sodium sulfide reaction leads to a considerable charge of the waste water.

Now, it was found that 4-amino-2,5-dialkoxybenzonitriles, especially those which contain alkoxy radicals having 1 to 4 carbon atoms, can be obtained in a technically simpler way, under more favourable conditions with respect to the ecology and with an improved yield by brominating 1-acylamino-2,5-dialkoxybenzenes, converting the 1-acylamino-2,5-dialkoxy-4-bromobenzenes so obtained by the reaction with copper-I-cyanide to the 4-acylamino-2,5-dialkoxybenzonitriles and then hydrolyzing the acylamino group. The "acyl" radical used herein is to be understood as one of a lower aliphatic carboxylic acid or an aromatic carboxylic acid, such as the benzoic acid substituted or unsubstituted in the nucleus.

The process of the invention is advantageously carried out by primarily brominating an acylamino-2,5-dialkoxybenzene as defined above, preferably the 1-acetylamino-2,5-dimethoxy- or -2,5-diethoxy-benzene, for example with hydrogen bromide and in the presence of oxidizing agents in aqueous solution or with bromine, advantageously in the presence of oxidizing agents, for example chlorine, concentrated sulfuric acid or oleum.

It is also possible to start from another 1-acylamino-2,5-dialkoxy benzene, for example a 1-formylamino-, 1-propionylamino or 1-benzoylamino-2,5-dialkoxy benzene.

The 1-acylamino-2,5-dialkoxy-4-bromobenzene is then reacted with copper-I-cyanide in the presence of a dissolving promoter for copper-I-cyanide, such as an organic base, for example, pyridine, piperidine, quinoline, cyclohexylamine, a nitrile, such as acetonitrile, propionitrile, benzonitrile or benzylcyanide, a carboxylic acid amide, such as formamide, dimethyl formamide, acetamide or dimethylacetamide, dimethyl sulfoxide or N-methylpyrrolidone. The reaction is advantageously carried out in an inert solvent, for example, a low-aliphatic alcohol, such as ethanol, butanol, in toluene, nitrobenzene, di- or trichlorobenzene, or in the dissolving promoter itself.

The 4-acylamino-2,5-dialkoxybenzonitriles so obtained which are defined above are then hydrolyzed in the heat, advantageously by a treatment with aqueous acids, such as hydrochloric acid or sulfuric acid.

According to the process of the invention, the 4-amino-2,5-dialkoxybenzonitriles are obtained in very high purity.

Compared with the known process, the process of the invention requires less operational steps and a reduced expenditure of apparatus. It supplies higher yields, reduces the charge of the waste water to a considerable extent and is less expensive.

The following example illustrates the invention; the relationship of the parts by weight to the parts by volume is the same as the kilogram to the liter, the parts being by weight unless stated otherwise.

EXAMPLE

300 Parts of 1-acetylamino-2,5-dimethoxybenzene were introduced at about 5°C in 1500 parts of 95 % sulfuric acid while stirring, 127 Parts of bromine were added dropwise at about 5°C with outside cooling. The mixture was stirred at 20°C for about 3 hours, 6000 parts by volume of water were added dropwise (a temperature of 25°C is not to be exceeded), the precipitate was suction-filtered and dried. 381 parts of 1-acetylamino-2,5-dimethoxy-4-bromobenzene ( = 90.4 % of the theory) were obtained.

A mixture of 100 parts of 1-acetylamino-2,5-dimethoxy-4-bromobenzene, 722 parts of nitrobenzene, 30 parts of dimethylformamide and 41 parts of copper-I-cyanide were heated at 200°C for 8 hours, while stirring.

After cooling to 70°–80°C the nitrobenzene was blown out with steam. The filtrate was cooled to 20°–25°C and the precipitate was suction-filtered after stirring for one hour.

The crude moist product was stirred twice each with 500 parts by volume of water and 500 parts of 25 % ammonia at room temperature for two hours in order to reduce the content of copper compounds, thereafter suction-filtered, washed with water until neutral and dried at 60°C.

63 Parts of 4-acetylamino-2,5-dimethoxybenzonitrile ( = 78.5 % of the theory) were obtained which melted at 165°–168°C.

50 Parts of 4-acetylamino-2,5-dimethoxybenzonitrile were introduced in 200 parts by volume of water and 115 parts of 30 % hydrochloric acid and heated at 90°C within two hours and a half while stirring.

After the addition of a further 400 parts by volume of water the mixture was again heated to 90°C, the solution was clarified while hot after the addition of 5 parts of active charcoal and 5 parts of kieselguhr, the filter residue was washed with 50 parts by volume of hot water and the filtrate was adjusted at pH 5 by adding dropwise 125 parts of a 33 % sodium hydroxide solution with simultaneously cooling. After cooling to + 10°C stirring followed at that temperature for 1 hour, the precipitate was suction-filtered, washed with 600 parts by volume of water and dried at 60°C.

35.5 Parts of 4-amino-2,5-dimethoxybenzonitrile ( = 87.8 % of the theory) were obtained.

In an analogous manner, the 4-amino-2,5-dimethoxybenzonitrile was obtained in a yield of 85 % of the theory.

What is claimed is:

1. A process for preparing a 4-amino-2,5-di($C_1$–$C_4$) alkoxybenzonitrile which comprises first brominating a 1-acylamino-2,5-dialkoxybenzene with hydrogen bromide in the presence of an oxidizing agent in aqueous solution or with bromine in sulfuric acid, then converting the 1-acylamino-2,5-dialkoxy-4-bromo-benzene so obtained, by the reaction with copper-I-cyanide in an inert solvent and in the presence of a dissolving promotor for the copper-cyanide to the 4-acylamino-2,5-dialkoxy-benzonitrile, and subsequently hydrolyzing the acylamino group.

* * * * *